(12) United States Patent
Zuluage

(10) Patent No.: US 9,265,426 B2
(45) Date of Patent: Feb. 23, 2016

(54) SANITARY COVER SLEEVE FOR MEDICAL DEVICE WITH ELECTRICAL CONTACT

(71) Applicant: Andres Felipe Zuluage, Houston, TX (US)

(72) Inventor: Andres Felipe Zuluage, Houston, TX (US)

(73) Assignee: Remicalm, LLC, Houston, TX (US)

( * ) Notice: Subject to any disclaimer, the term of this patent is extended or adjusted under 35 U.S.C. 154(b) by 168 days.

(21) Appl. No.: 13/694,512

(22) Filed: Dec. 7, 2012

(65) Prior Publication Data

US 2013/0150729 A1    Jun. 13, 2013

Related U.S. Application Data

(60) Provisional application No. 61/630,365, filed on Dec. 9, 2011, provisional application No. 61/689,203, filed on May 31, 2012.

(51) Int. Cl.
*A61B 5/00* (2006.01)

(52) U.S. Cl.
CPC ......... *A61B 5/0088* (2013.01); *A61B 2562/247* (2013.01)

(58) Field of Classification Search
CPC .................. A61B 5/0088; A61B 2562/247
USPC ............................................. 600/407, 476
See application file for complete search history.

(56) References Cited

U.S. PATENT DOCUMENTS 4,476,872 A * 10/1984 Perlin ........................... 600/380
4,545,375 A * 10/1985 Cline ............................. 606/42

* cited by examiner

*Primary Examiner* — Bo J Peng
(74) *Attorney, Agent, or Firm* — Elizabeth R. Hall

(57) ABSTRACT

A disposable cover sleeve serves is used to cover an electronic or optical medical device used for patient examination and/or treatment. The cover sleeve provides an environmental barrier for the medical device during patient examination to prevent environmental cross-contamination of different patients examined with the same medical device. The cover sleeve has an integrated device activation means such as a flexible contact bridge. The device activation means has an open and closed position. The open position is not in physical, electronic or magnetic contact with the control electronics of the medical device; whereas, the closed position closes a field or circuit between a first and second contact to selectively actuate or provide input to the control electronics that communicate with the radiation source.

13 Claims, 7 Drawing Sheets

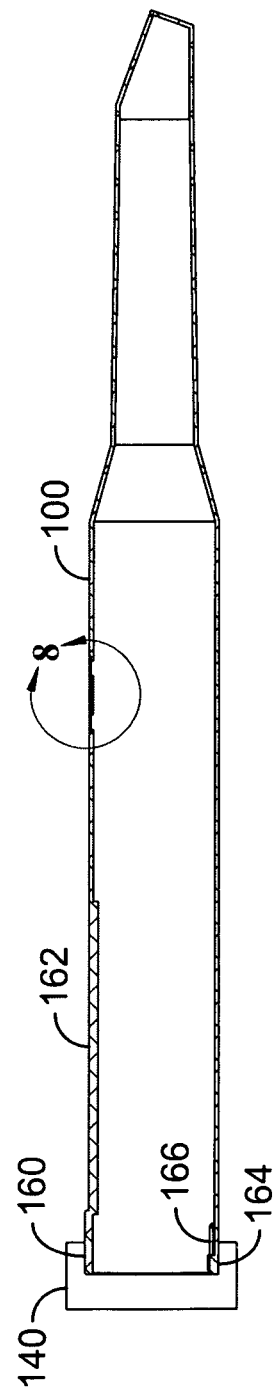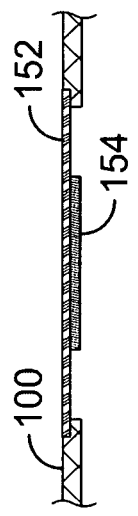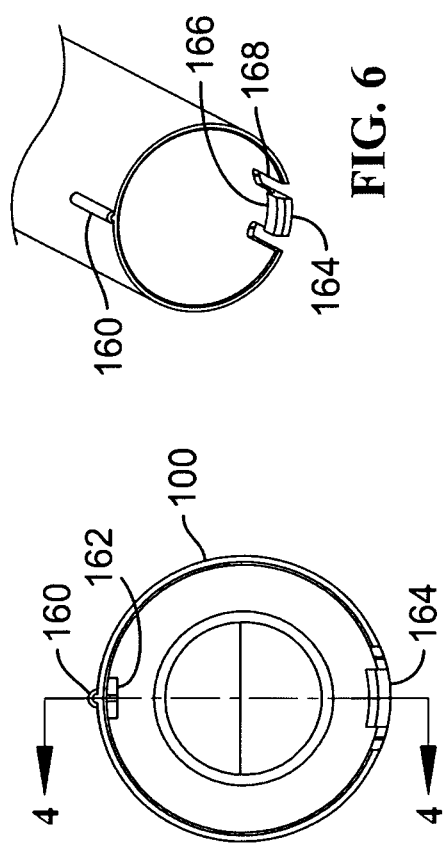

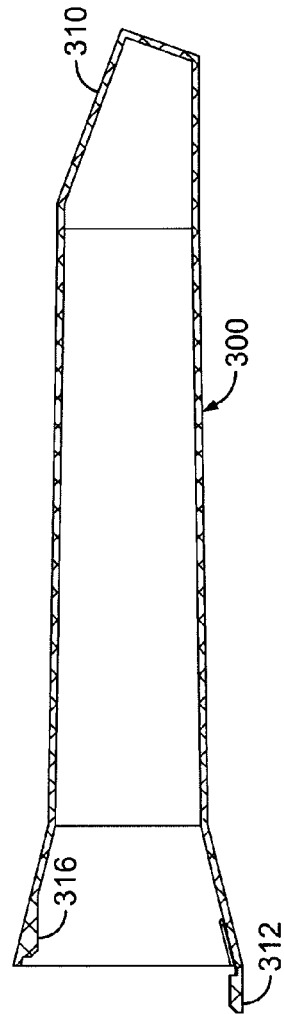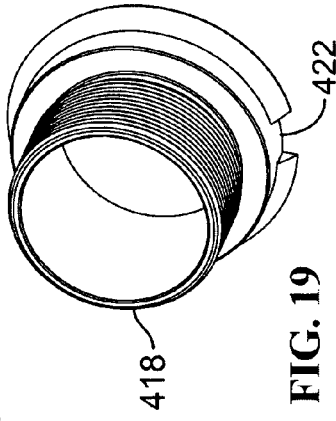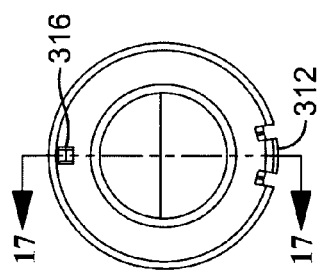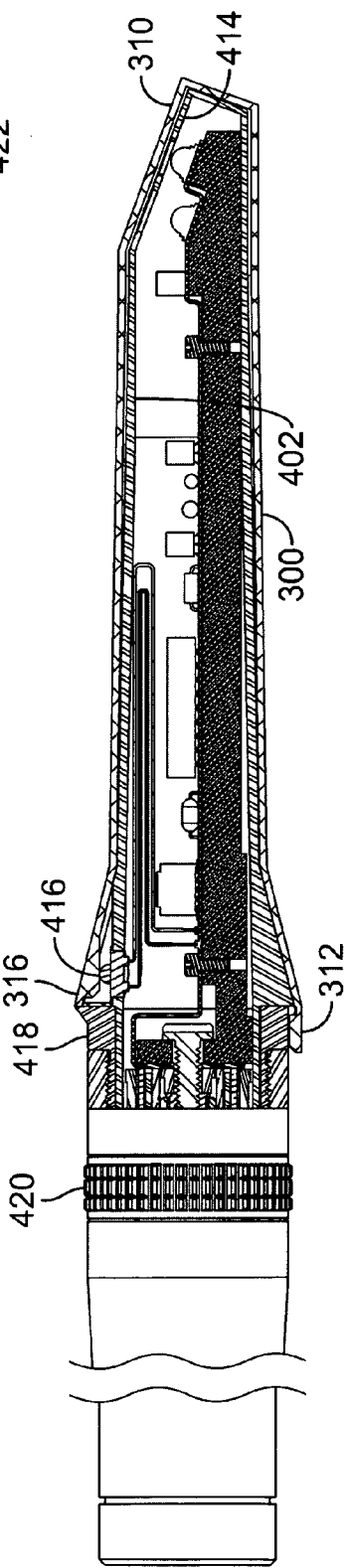
FIG. 17
FIG. 19
FIG. 16
FIG. 18

SANITARY COVER SLEEVE FOR MEDICAL DEVICE WITH ELECTRICAL CONTACT

CROSS-REFERENCE TO RELATED APPLICATIONS

This application claims the priority of prior Provisional U.S. Patent Application Ser. No. 61/630,365 filed on Dec. 9, 2011 and entitled "Sanitary Cover Sleeve for Medical Device with Electrical Contact." This application also claims the priority of prior Provisional U.S. Pat. No. 61/689,203 filed on May 31, 2012 and entitled "Sanitary Cover Sleeve for Dental Instrument." Each of these provisional applications is hereby incorporated by reference herein in its entirety.

FIELD OF THE INVENTION

The invention relates to a disposable cover sleeve for covering a medical device or tool used for patient examination and/or treatment. More particularly, the present invention relates to a disposable cover sleeve having an integrated electrical contact and, in one embodiment, a selectively transmissive window.

DESCRIPTION OF THE RELATED ART

Clinicians and dentists have been aware for years that the repeated handling of small medical devices or probes by medical personnel without proper sterilization can cause the spread of contagious diseases. The pathogenic agents responsible for spreading such contagious diseases are often borne in or on the body fluids and/or tissues that come into contact with external surfaces of the medical device or the gloved or ungloved hands of the medical personnel using the device. For example, the hepatitis virus and the acquired immunodeficiency virus have been found to be carried in or on body fluids and/or tissues.

In the environment in which clinicians and dental practitioners work (i.e. inside the mouth and other bodily cavities), they come into constant contact with bodily fluids such as saliva, blood and tissue exudate. Small electronic and optical medical devices or probes that are used to screen tissues or bodily cavities for diseased tissues often come into contact with and are contaminated with these bodily fluids. If these devices are not properly sterilized before each use, the medical device can itself become a carrier of disease.

While it is possible to remove and discard the protective gloves used by medical and dental personnel, cleaning and sterilizing the exterior of sensitive electronic medical devices has become a serious problem because of their specialized construction and because multiple cycling of electronic medical devices through the sterilization process can significantly shorten the useful lifetime of that medical device.

There is a continuing need to provide a disposable protective pathogenic barrier for electronic and optical medical devices or probes which may be inserted into the mouth or body of a patient to significantly reduce or prevent the spread or cross-contamination of contagious, communicable diseases.

SUMMARY OF THE INVENTION

One embodiment of the invention provides a cover sleeve comprising: a cover sleeve body having a first closed end, a second open end, and a lumen, wherein the cover sleeve body is designed to provide a close fit to a medical device when the medical device is inserted into the lumen of the cover sleeve body; a transmissive window that is transparent to radiation emitted by a radiation source positioned within the medical device; and a deflectable contact bridge integrally attached to the cover sleeve body, the contact bridge positioned to physically contact a first contact and a second contact exposed on an outer surface of the medical device when a force is selectably applied to the contact bridge, wherein the physical contact between the contact bridge and the first and second contacts closes a circuit between the first and second contacts.

In an alternative embodiment, the present invention is a medical examination assembly, comprising: (a) a medical device having a radiation source and an elongate body, wherein the body has a transmission window aligned with the radiation source and a pair of contacts exposed on an outer surface thereof; and (b) a cover sleeve including a cover sleeve body having a first closed end, a second open end, and a lumen, wherein the cover sleeve is designed to provide a close fit over an entire length of the medical device when the medical device is fully inserted into the lumen of the cover sleeve body; a sealable end that fits over the open end to provide a pathogenic barrier for the medical device when the medical device is fully enclosed in the cover sleeve sealed with the sealable end; and a contact bridge having an open position and a closed position, wherein when a user selectably moves the contact bridge into the closed position, the contact bridge interacts with the pair of contacts to close a circuit between the pair of contacts to actuate the medical device.

Yet another embodiment of the present invention is a medical examination assembly, comprising: a medical device having a radiation source and an elongate body, wherein the body has a transmission window aligned with the radiation source and a switch on an outer surface of the medical device; and a cover sleeve, the cover sleeve having a first closed end, a second open end, and a lumen, wherein the cover sleeve is designed to provide a close fit to the medical device when the medical device is inserted into the lumen of the cover sleeve, and wherein said cover sleeve includes a switch activation mechanism for depressing the switch on the medical device as the medical device is inserted into the lumen of the cover sleeve; whereby, whenever the switch is depressed the medical device is actuated.

The foregoing has outlined rather broadly several embodiments of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed might be readily utilized as a basis for modifying or redesigning the structures for carrying out the same purposes as the invention. It should be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIG. 5 shows a cross-sectional end view of the medical screening device installed in the cover sleeve.

FIG. 6 shows an oblique view of the latch of the cover sleeve.

FIG. 7 is a cross-sectional side view of the cover sleeve.

FIG. 8 is close up view of a contact bridge inset in the cover sleeve.

FIG. 16 is an end view of the second embodiment of the cover sleeve from FIG. 14.

FIG. 17 is a side cross-sectional view of the cover sleeve from FIG. 14.

FIG. 18 is a side cross-sectional view of the embodiment of the medical device with the cover sleeve of FIG. 11.

FIG. 19 is a perspective view of an assembly screw from the medical device of FIGS. 12 and 15.

DESCRIPTION OF SPECIFIC EMBODIMENTS OF THE INVENTION

Figure 1:
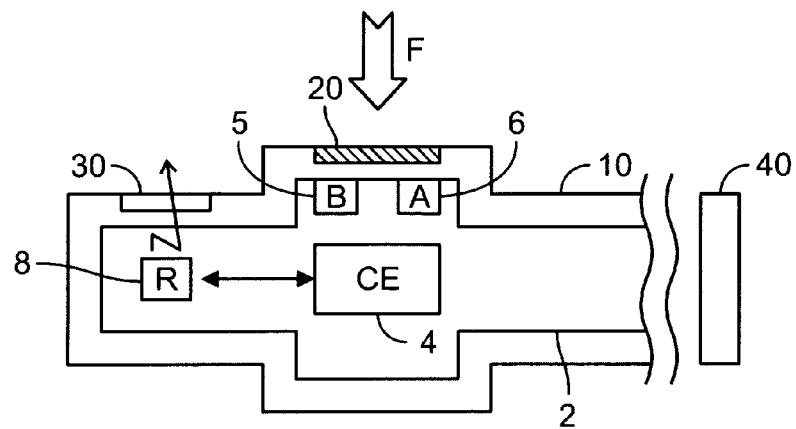
FIG. 1 is a schematic of an end of a medical device having a radiation source and a first and second contact covered by a protective cover.

The invention relates to a disposable protective pathogenic barrier for various types of medical devices, including electronic and optical medical devices or probes which may come into contact with body fluids and/or tissues. In particular, although certain embodiments of the invention are described herein involving dental instruments for insertion into patients' mouths, those of ordinary skill in the art will appreciate that the invention may be advantageously practiced in connection with other types of medical instruments and devices. Certain embodiments of the invention include a disposable pathogen barrier for placement over and in proximate contact with a medical device that has a radiation source or a light emitting means. The disposable pathogenic barrier over such a medical device significantly reduces the spread of communicable and infectious diseases which may be transmitted by or through contact with human body fluids and tissues during a first and subsequent use of the medical device in conjunction with the treatment of two or more patients. The disposal of the disposable cover sleeve after each use eliminates the need for repeated sterilization of the medical device between such uses for two or more patients.

The disposable pathogen barrier or cover sleeve is comprised of an elongated body having an aperture at a first end thereof. Preferred embodiments are designed to fit over all of the surface of the medical device that may come into contact with patient tissues directly or indirectly. Other embodiments of the cover sleeve are designed to fit over a substantial portion of the surface of the medical device and be in close contact with the outer surface of the medical device. The aperture at the first end of the cover sleeve is designed to allow a first end of the medical device to enter the cover sleeve and move through a lumen or bore of the cover sleeve to a second closed end of the cover sleeve.

Embodiments of a disposable cover sleeve are described that cover the portion of an electronic or optical medical device and/or the entire optical medical device used for patient examination. For example, the cover sleeve 10 would be suitable for fitting over the outer surface of the dental screening device described in U.S. Patent Application Publication No. US 2010-0036260 A1, the entirety of that publication is herein incorporated by reference.

The use of a disposable cover sleeve during a patient examination protects the screening device from coming into intimate contact with the patient directly or indirectly. Thus, after performing a screening examination of a first patient with the optical medical device, the first disposable cover sleeve can be properly disposed of as biological waste material. A new disposable cover sleeve can then be placed on the optical medical device and used to perform an examination of a second patient without having to disinfect the device.

Preferred embodiments of the cover sleeve are molded from a strong optically clear grade of plastic with little or no autofluorescence when illuminated with ultraviolet, visible, near-infrared, or infrared light. The cover sleeve 10 can be manufactured of a material with low thermal and electrical conductivity such as latex, polyethylene, polycarbonate, polyurethane, styrene, PTFE, phenolic, PEG, PETG, PVDF, acrylic, ultem, PVC, CPVC, PET, PBT, PBAX, ABS, PLA, cyclic olefin copolymers (coc), zeonex, acetal, nylon, mylar, natural rubber or other organic and inorganic polymers and materials.

Such cover sleeves not only serve as a sanitary cover for the optical medical device, but they also have low thermal conductivity that enhance patient comfort by insulating patient contact surfaces from any heat generated by the device operation, and from any materials with high thermal conductivity on the instrument surface such as metals which may feel uncomfortably cold when touched. This would similarly enhance user/provider comfort.

For example, devices using LED or laser illumination sources often generate a lot of heat and it is important that the patient is not burned or made uncomfortable during the examination. Furthermore, since preferred embodiments of the cover sleeve cover the entire optical medical device, including where it is held by the physician or clinical personnel, the cover sleeve also insulates the handle of the device to protect the user of the device from any discomfort by any heat buildup. The cover sleeve 10 may additionally serve to enhance any electrical insulation to the patient and user necessary given the instrument's electrical powering scheme; and serve to enhance electromagnetic shielding of any radiation generated that may interfere with other instruments.

The cover sleeve 10 that is schematically illustrated in FIG. 1 has an integrated contact bridge 20 that can be selectively operated to activate a desired function of the medical device. The cover sleeve 10 shown in FIG. 1 has a selectively transmissive window 30, but other embodiments of the cover sleeve 10 may include more than one selectively transmissive window 30. The cover sleeve provides an environmental barrier for the medical device during patient examination to prevent environmental cross-contamination of different patients examined with the medical device.

A schematic representation of an electronic medical device 2 covered by the cover sleeve 10 is shown in FIG. 1. The medical device 2 includes control electronics 4 in communication with a first contact 5, a second contact 6, and a radiation source 8. Whenever the contact bridge 20 is in physical, electronic or magnetic contact with the first contact 5 and the second contact 6, the contact bridge 20 closes a field between the first and second contact which is necessary to actuate and/or provide input to the control electronics 4. The closed position may close an electrical circuit or magnetic circuit or actuate a secondary physical device that closes an electrical or magnetic circuit.

The radiation source 8 is an energy source such as an optical source (e.g., infrared, near-infrared, visible, ultraviolet or fluorescent light), an electro-magnetic source (e.g., x-rays, gamma rays, or radio waves), or a pressure source (e.g., audio or ultrasound). The activation and/or conditioning of the radiation source 8 are selectively determined by the control electronics 4.

The cover sleeve 10 is preferably a flexible elastomeric material that provides a close fit to the medical device 2. The cover sleeve 10 protects the medical device 2 from the environment. The cover sleeve 10 provides a barrier against environmental contamination and pathogenic agents, as well as a thermal insulator.

Figure 2A:
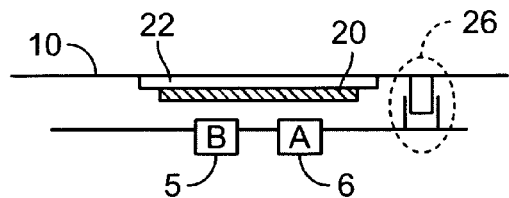
FIG. 2A is a schematic view of the contact bridge in an open position.
Figure 2B:
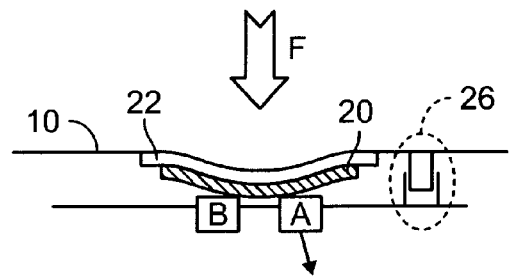
FIG. 2B is a schematic view of the contact bridge in a closed position.

The cover sleeve 10 has a contact bridge 20 inset in the cover sleeve 10. The contact bridge 20 is seen in more detail in FIGS. 2A and 2B. FIG. 2A shows the contact bridge 20 in an open position and FIG. 2B shows the contact bridge 20 in a closed position. Alternatively, it should be noted that when the contact bridge is in the open position that the contact bridge may be in contact with one of the contacts (either the first contact 5 or the second contact 6) but not both. The contact bridge is designed to interact with both the first contact 5 and the second contact 6 simultaneously when the contact bridge 20 is in the closed position and not to interact with either the first contact 5 or the second contact 6 when the contact bridge is in the open position.

The contact bridge 20 is typically mounted on the underside of a flexible layer 22 inserted into the external surface of the cover sleeve 10. The contact bridge 20 is positioned between the flexible layer 22 and the first contact and second contact of the medical device 2. However, the flexible layer 22 may not be an independent element of cover sleeve 10 as it may be made of the same material be a part of or integrally integrated with either the cover sleeve 10 or the contact bridge 20.

Whenever the cover sleeve 10 is fitted onto the medical device 2 and no force is applied to the external surface of the flexible layer 22 as seen in FIG. 2A, the contact bridge 20 is in its open position. In its open position the contact bridge 20 is not in physical, electronic or magnetic contact with the first and/or second contact and is centered above the first and second contacts of the medical device. When the contact bridge 20 is in the open position there is an open circuit or field between the first contact 5 and the second contact 6 and no communication with the control electronics 4.

When force is applied to the external surface of the flexible layer 22, the flexible layer 22 is depressed and the contact bridge 20 comes into physical, electronic or magnetic contact with both the first contact 5 and the second contact 6 as illustrated in FIG. 2B. When the contact bridge 20 is in contact with the first and second contact of the medical device 2, the contact bridge 20 is in its closed position and closes an induction force field, a magnetic circuit or an electrical circuit to actuate the control electronics 4.

Preferred embodiments of the cover sleeve 10 have an optional contact bridge alignment mechanism 26 to ensure that the contact bridge 20 is correctly aligned over the first and second contact of the medical device when the cover sleeve is emplaced over the medical device 2. One embodiment of the contact bridge alignment means 26 is schematically illustrated in FIG. 2A and FIG. 2B. However, the positioning of the cover sleeve 10 over the medical screening device 2 may not need assistance by a positioning means. More specifically, the cover sleeve 10 may be designed such that the first and second contacts, the contact bridge, and the emission window are insensitive to rotational orientation.

One safety feature generally incorporated into the medical device is that the medical device is not operable unless the cover sleeve 10 is emplaced over the medical device. Thus, the environmental barrier provided by the cover sleeve 20 must be properly positioned over the medical device so that the contact bridge 20 can actuate the control electronics of the medical device when the contact bridge 20 is in physical, electronic or magnetic contact with the first and second contacts of the medical device.

The cover sleeve 10 also includes a transmissive window 30. The transmissive window 30 overlies and is centered over the radiation source 8. The transmissive window 30 is transparent to the energy emitted from the radiation source 8. For example, if the radiation source is a light source, the transmissive window freely passes the light rays from the radiation source without distortion, interruption or light wavelength shifting.

Figure 3:
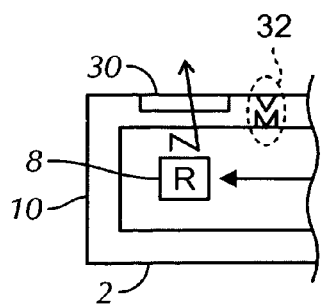
FIG. 3 is a schematic view of the transmissive window centered over the radiation source.

Some embodiments of the cover sleeve 10 and the medical device 2 have a transmissive window alignment mechanism 32 to ensure that the transmissive window 30 is correctly aligned and centered over the radiation source 8 when the cover sleeve is emplaced over the medical device 2. One embodiment of the transmissive window alignment means 32 is schematically illustrated in FIG. 3.

Preferred embodiments of the cover sleeve 10 have a closed end and an open end with a central bore designed to be a tight fit over the medical device. The cover sleeve 10 substantially mirrors the shape of the medical device 2 that the cover sleeve fits over. For example, the cover sleeve 10 is typically installed over the medical device 2 by inserting one end of the medical device 2 into the open end of the cover sleeve 10 and aligning the contact bridge 20 with the first contact 5 and the second contact 6, as well as aligning the transmissive window 30 with the radiation source 8 of the medical device 2.

Once the medical device 2 is inserted all the way into the cover sleeve 10, the open end of the cover sleeve 10 is sealed with a sealable end 40. The sealable end is sealingly mounted on the open end of the cover sleeve 10 by a variety of attachment means such as threads, latches, adhesives or other means.

A First Embodiment of the Cover Sleeve

Figure 4:
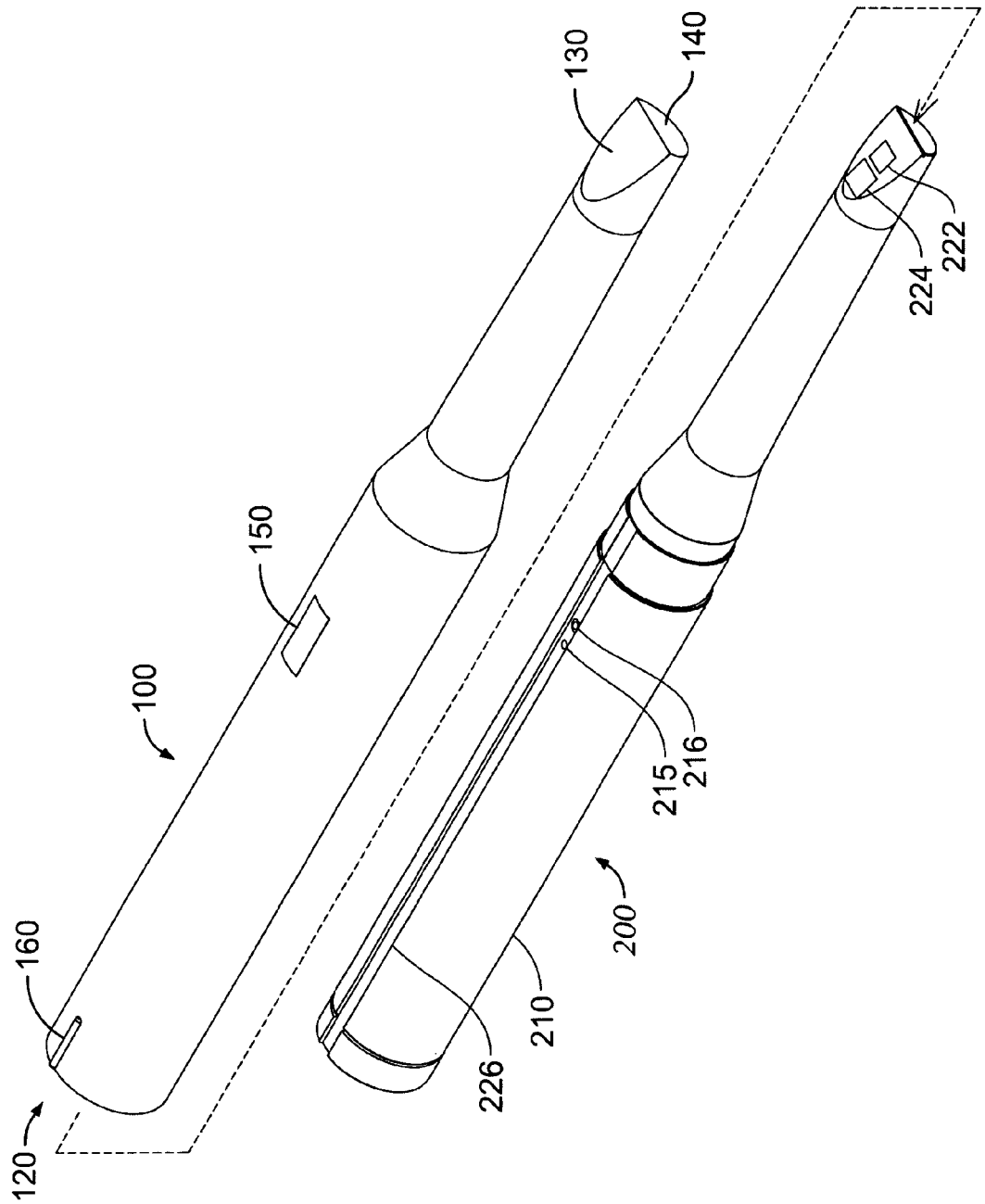
FIG. 4 is a diagonal view of the cover sleeve and a medical screening device.

FIG. 4 shows a diagonal view of a first embodiment of the sanitary cover sleeve 100 designed to fit and protect a light emitting medical screening device. One embodiment of the medical screening device 200, shown in FIG. 4, is a battery powered illumination device used to screen for sites of diseased tissue.

The cover sleeve 100 has a closed end 140 and an open end 120 with a central bore designed to be a tight fit over the medical device 200. The cover sleeve 100 is elongated and substantially mirrors the shape of the medical device 200.

The cover sleeve 100 is installed over the substantially elongated medical device 200 by inserting the end of the medical device 200 having a first transmission window 222 and a second transmission window 224 into the open end 120 of the cover sleeve 100 and aligning the manual switch cover 150, which contains a contact bridge 20, with the first contact 215 and the second contact 216.

The cover sleeve 100 is sufficiently elongated to cover the entire external surface of the medical device 200. Once the medical device 200 is inserted all the way into the cover sleeve 100, the open end 120 of the cover sleeve 100 is sealed with a sealable end 140. One example of a mountable sealable end 140 is shown in FIG. 7. The illustrated sealable end 140 has a slip fit to the open end 120 with an optional slot that fits over the centerline indicator 160 of the cover sleeve 100. Once the sealable end 140 is in place the medical device 200 is totally protected by the environmental barrier provided by the cover sleeve 100.

The cover sleeve 100 has a close fit to the body of the medical screening device 200 and is made of a material that is not electrically or thermally conductive. The cover sleeve 100 has a manual switch cover 150 embodied in the cover sleeve 100. The manual switch cover 150 includes a contact bridge 152 and an integrated flexible layer 154. The manual switch cover 150 communicates with the control electronics of the medical screening device whenever the switch cover 150 is depressed so that the contact bridge 20 mounted on the underside of the switch cover 150 physically contacts the first contact 214 and the second contact 1216 on the external surface of the medical screening device 200. The connection of the first and second contact with the contact bridge closes a circuit or field between the two contacts to actuate the control electronics of the device as described in more detail below.

A transparent window, or light emission face 130, of the installed sleeve 100 is parallel to and only slightly spaced apart from the light emission windows on the insertable end of the medical screening device 200 so that the light emitted by the medical screening device can freely pass through the cover 100 without distortion.

The cover sleeve 100 is installed by inserting the light emitting end of the medical screening device 200 in the open end 120 of the cover 100, aligning the flat light emission face 130 of the cover with the light emission windows of the medical screening device, and then continuing insertion of the tool until the latch 164 at the open end 120 of the cover 200 engages with the transverse rear end of the device 200.

The proper positioning of the cover sleeve 100 over the medical screening device may be assisted by various positioning means such as the optional alignment slots and/or the latch on the cover sleeve 100 shown in FIGS. 4 to 7. Alignment slots, protrusions, or notches may be used on the external surface of the medical screening device to ensure the proper longitudinal and/or rotational alignment of the cover sleeve with the medical screening device. For example, an interior alignment ridge 162 on the cover sleeve 100, such as seen in FIG. 5, can be engaged in an alignment slot 226 on the medical screening device to ensure proper positioning of the cover sleeve 100. In addition, an optional external centerline indicator ridge (such as seen in FIGS. 4 and 5) on the exterior of the cover sleeve aids visual alignment of the cover sleeve 100 to the body of the medical screening device 200.

A latch 164 on the cover sleeve 100 may also be employed to ensure proper positioning of the cover sleeve on the medical screening device. An example of such a latch is seen in FIGS. 5 and 6. The latch 164 illustrated on the cover sleeve 100 is a relatively short flexible piece with its outer diameter being about the same as that of the cylindrical portion of the cover sleeve 100. However, the latch 164 has an inwardly facing upset 166. The inner radius of the inward upset 166 portion of the latch is less than the outer radius of the handle of the medical screening device.

One embodiment of the latch 164 is integral with the cover sleeve 100, but it is separated in the circumferential direction by a pair of axially short narrow mirror image offset parallel stress relief slots 168. These slots permit the latch to radially flex outwardly to pass over the handle of the tool. The elastic properties of the cover sleeve 100 cause the deflected latch 164 to rebound inwardly when the latch upset 166 passes over the transverse end of the medical device 200. The latch 164 can be released and the cover sleeve 100 removed with low levels of force to deflect the upset 166 portion of the latch 164 out of interference with the transverse end of the medical screening device 200.

Figure 10:
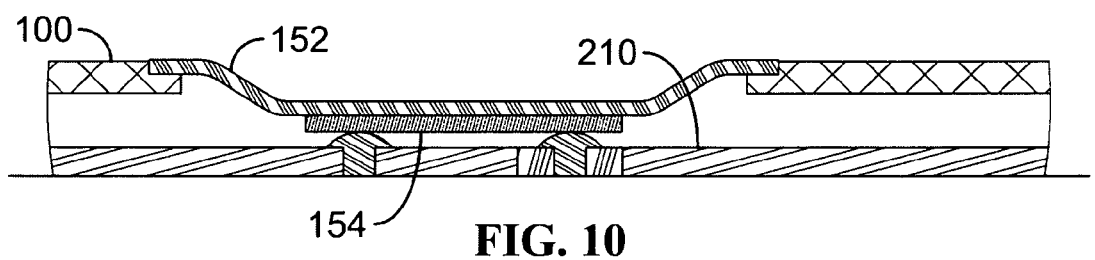
FIG. 10 shows the contact bridge of the first embodiment of the cover sleeve in a closed position.

As seen in FIGS. 4, 8 and 10, a stepped rectangular window is cut through the body of the cover sleeve and aligned with the alignment ridge. The inner portion of the window is smaller than the outer portion and is symmetrical with the outer portion of the window. A flexible cover 152 is mounted in the outer portion of the window so that it is externally flush with the outer surface of the medical device 200. A contact bridge 154 is bonded or adhesively attached to the interior side of the flexible cover 152.

The contact bridge 154 is typically shorter and narrower than the through portion of the window. Generally the contact bridge 154 is centrally placed in the through portion of the window. The flexibility of the flexible cover 152 permits radially inward displacement of the contact bridge 154 by selectably applied low levels of finger pressure.

Control electronics in the medical screening device 200 can take many configurations. The control electronics are actuated with the physical, electronic or magnetic contact of the contact bridge 154 with the first contact 215 and the second contact 216.

Figure 9:
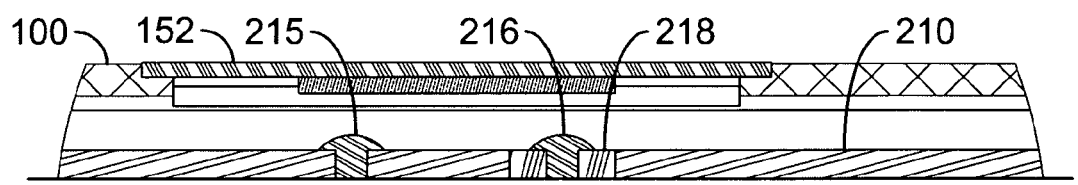
FIG. 9 shows the contact bridge of a first embodiment of the cover sleeve in an open position.

One example of a contact bridge 154 and the two contacts as illustrated in FIGS. 9 and 10. The two conductive contacts radially penetrate a conductive housing 210 of the medical device 200. The first contact 215 has its external head exposed to the conductive housing 210 that is part of the negative circuitry. The second contact 216 is insulated from the conductive housing 210 by an insulating grommet 218. The second contact 216 has its exterior head extending radially outward from the insulating grommet by about the same amount as the first contact 215. On its inner end, the second contact 216 is aligned with the positive circuitry of the device 200.

As seen in FIG. 10, the flexible cover 152 can be selectably depressed inwardly in order to physically contact both the first contact 215 and second contact 216 with the conductive contact bridge 154. The circuitry of the medical device 200 responds to the depression of the contact bridge 254 to the first and second contacts as shown in FIG. 10 by energizing the radiation source of the device. Operation of the device 200 is thus precluded when the cover sleeve 100 with the contact bridge 154 is removed.

A Second Embodiment of the Cover Sleeve

Figure 11:
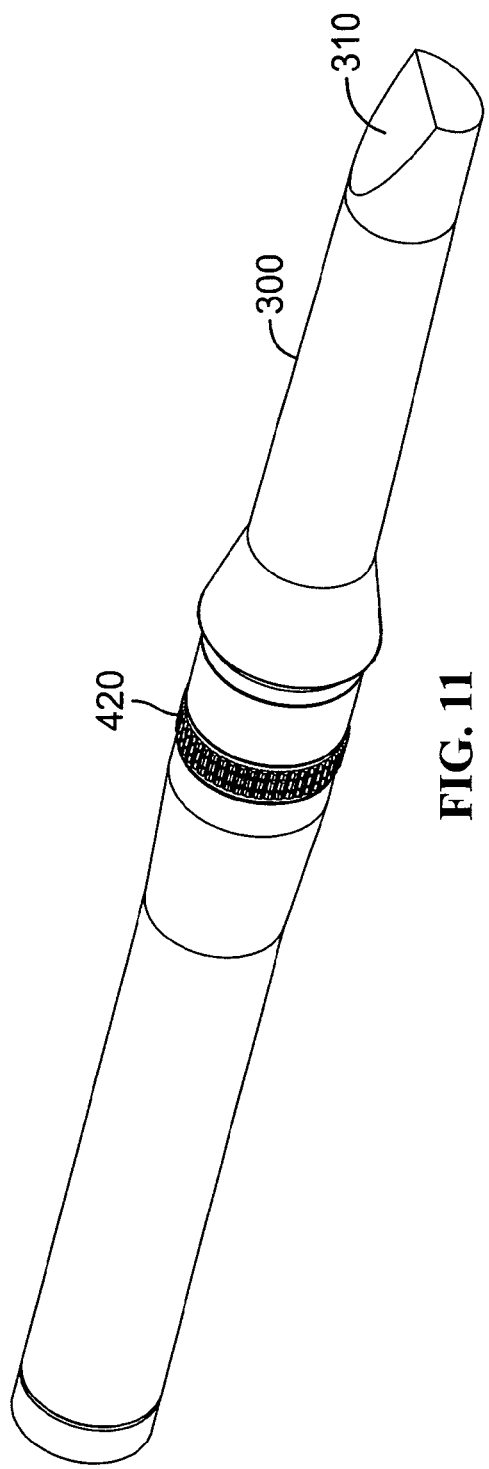
FIG. 11 is a perspective view of a medical device with a cover sleeve in accordance with an alternative embodiment of the invention.
Figure 13:
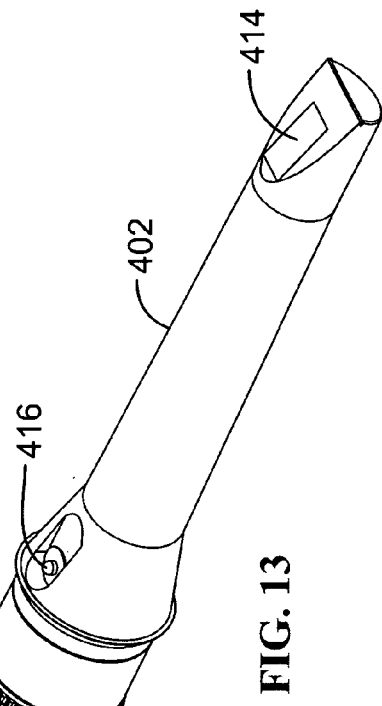
FIG. 13 is a perspective view of one embodiment of the medical device shown in FIG. 11 without the cover sleeve.

FIGS. 11 and 13 show two different diagonal views of a second embodiment of a cover sleeve 300 installed on a medical device. The sleeve 300 has a close fit to the end of the device 400 which mounts the radiation source 8.

Figure 12:
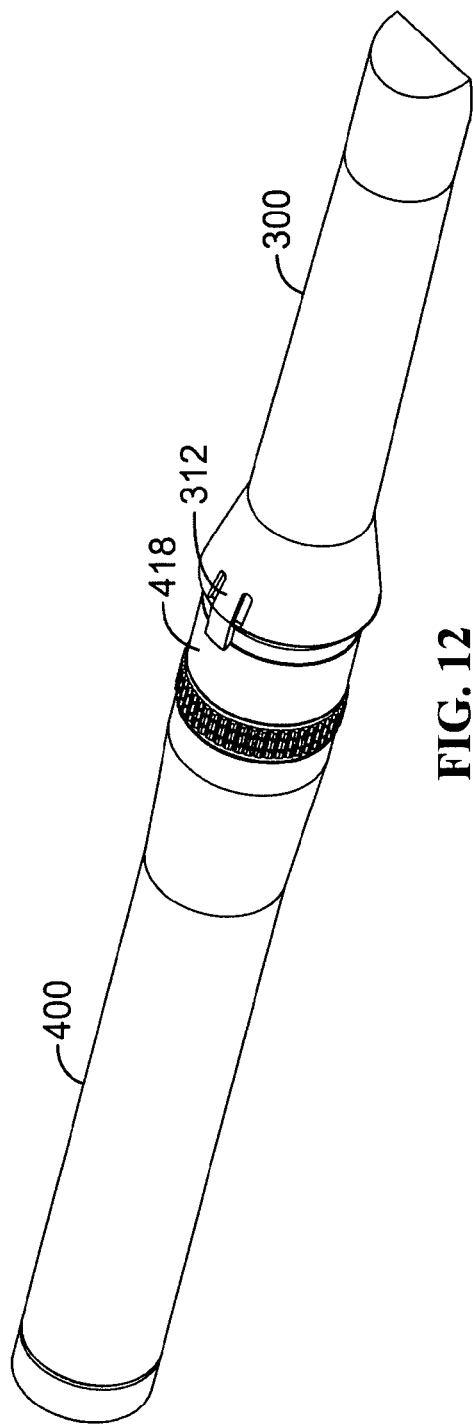
FIG. 12 is an alternative perspective view of the medical device and cover sleeve from FIG. 11.
Figure 15:
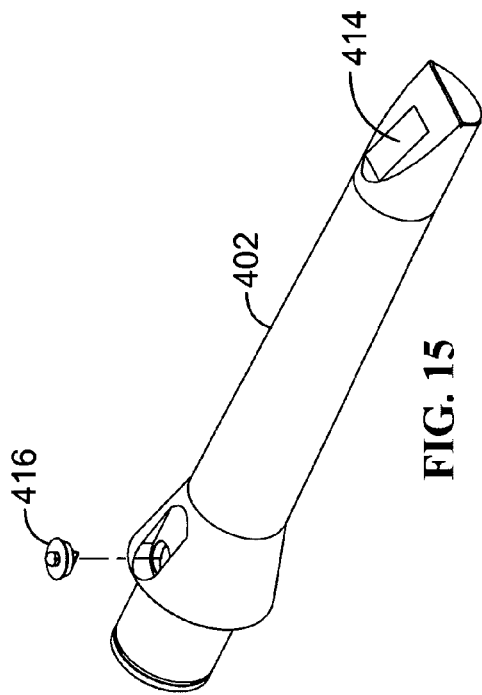
FIG. 15 is a perspective view of the head portion of the medical device shown in FIG. 13.

FIG. 12 shows one embodiment of the device 400 without the sleeve 300 installed. The device 400 has a head 402 and a handle 404 which is connected to the head via an assembly screw 418. The device 400 includes an optically transparent window 414, located in a planar surface of the device head 402, as seen in FIGS. 12 and 15. FIG. 12 shows the device 400 with a switch 416 which is radially mounted in a recess in a relatively thick radially outwardly upset section of the head 402 proximal where the head 402 attaches to the handle 404 of the device 400. FIG. 18 is a longitudinal sectional view of one embodiment of the head 402 of the device with the sanitary sleeve 300 installed.

Figure 14:
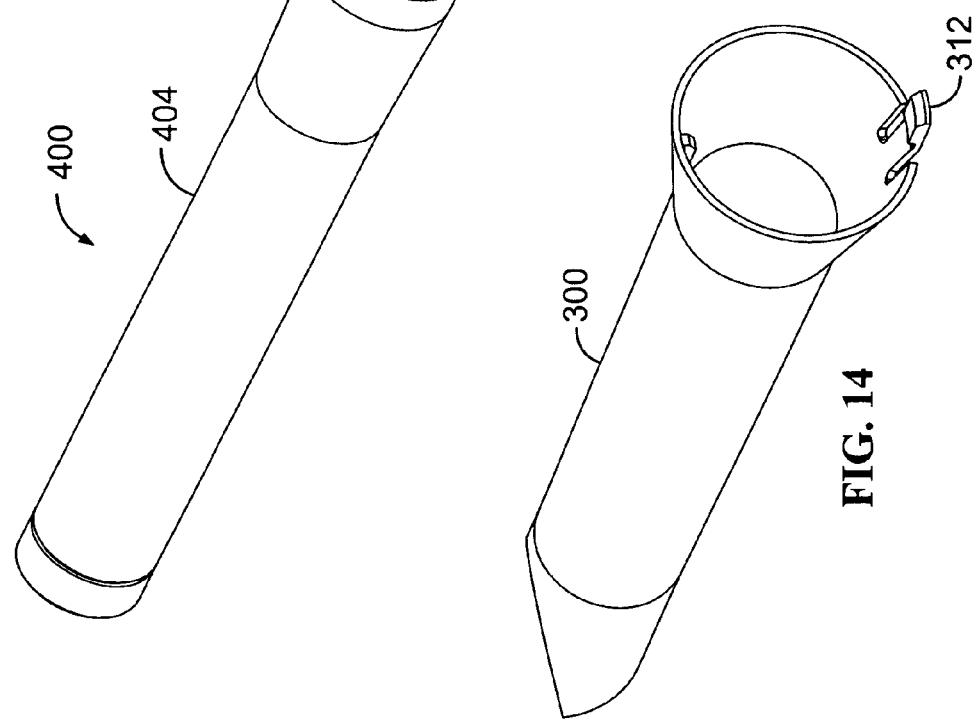
FIG. 14 is a rear perspective view of a second embodiment of the cover.

The cover sleeve 300, shown in FIGS. 14, 16 and 17, is shaped similar to the device for which it is designed to fit. The cover sleeve includes an optically transparent window 310, a switch activation means 316, and a latch 312. The transparent window 310 is optically transparent to the radiation emitted by the radiation source 8 of the device. The transparent window 310 of the installed sleeve 300 is positioned parallel to and only slightly spaced apart from a planar transmission window 414 covering the radiation source 8 of the device 400.

The device 0 has an on/off switch 416 mounted in the head 402. One embodiment of the switch 416 has two poles and is spring biased to a normally open position, but can be closed when its outwardly extending switch button is mechanically forced inwardly. When mounted in the head 402 of the device, the switch button extends radially outwardly along the longitudinal plane of symmetry of the device typically two lead wires attached to the poles of the switch 416 are attached at their other ends to contacts on the circuit board of the device, as seen in FIG. 18.

While the cover sleeve 300 is a relatively close slip fit to the device 400, the fit may not be sufficiently tight to ensure retention of the sleeve during use of the device. For this reason, a latch 312 is provided as shown in FIGS. 14 and 17. In order to permit ready engagement and disengagement of the cover sleeve 300, the material for the sleeve is selected to have a low bending modulus, while at the same time having adequate bending strength to withstand necessary deflections during latch opening and closing.

Referring to FIG. 16, the latch 312 is formed by having two spaced apart longitudinal slots extending from the open end of the cover sleeve a short distance into the body of the sleeve. The slots are basically symmetric about the longitudinal plane of symmetry of the sleeve. The region of the sleeve wall between the slots is extended outwardly from the transverse open end of the sleeve parallel to the part axis. The cylindrical inner radius of the extension is the same as the inner radius of the sleeve at its entry for a short distance.

At the end of this short extension, a transverse radially inwardly extending shoulder is formed by the radially inwardly extending thickening of the latch body. The thickened portion of the latch extends a short distance parallel to the sleeve axis. At its outer end, the latch has both internal and external bevels. The internal bevel permits engagement of the end of the latch by a fingernail or finger tip so that the latch can be deflected outwardly.

As seen in FIG. 19, the assembly screw 418 is notched to accommodate the latch. When the cover sleeve 300 is assembled onto the device 400, the latch 312 can be visually aligned with the notch 422 of the assembly screw 418 to ensure alignment of the parallel flat faces of the device transmission window 414 and the transparent window 310 of the cover sleeve. Alternatively, the alignment of the cover sleeve to the device can be done by visual reference to the alignment of the transmission window 414 and the transparent window 310.

The illustrated embodiment of the cover sleeve has a radially inwardly extending ridge-like switch actuation bar 316 located on the interior of the cover sleeve diametrically opposed to the position of the latch 312. The inner side of the switch actuation bar 316 is parallel to the sleeve axis, and its width is such that it ensures that it will fit in the switch recess machined in the device where the switch 416 is mounted, as shown in FIG. 15. The radially inward extension of the switch actuation bar 316 is such that when the sleeve 300 is properly positioned on the head 402 of the device 400, the switch button is sufficiently depressed to close the field between the contacts to actuate the device.

Once the device is actuated, the function of the device (e.g., the type and wavelength of emitted radiation) can be selected through the use of a secondary switch or remote control. One embodiment of a secondary function selection switch incorporated into the device 400 is a rotary switch 420 that is described in U.S. Pat. No. 8,178,800, the entirety of which is herein incorporated by reference. Another embodiment of the secondary function selection means might be a remote microprocessor.

The circuitry of the device is configured so that the radiation source 8 will not be activated to emit radiation unless the switch 416 is depressed by the switch actuation bar 316. This feature ensures that the tool cannot be operated without the cover sleeve in place.

In the various embodiments of the invention disclosed herein, the cover sleeve is designed so that the medical screening device can only be used with the cover sleeve in place over the device to serve as an environmental barrier. Once the medical screening device has been used to screen one patient, the cover sleeve is removed and replaced with a new sterile cover sleeve. Replacing the cover sleeve with each use of the medical device ensures that a patient is not inadvertently exposed to contaminants or pathogenic agents from another patient.

The cover sleeve can be made such that disengaging it will cause the environmental barrier and/or the contact bridge to break, or cause damage to the cover sleeve's alignment features. For example, an adhesive sealing used to seal the sleeve shut can be made strong enough that the cover sleeve must be torn to remove it. Alternatively, the alignment features of the cover sleeve may be made of an easily breakable plastic such that the breakable plastic alignment features are simple to insert but must be broken to remove. The destruction of the sleeve with its removal will prevent multiple uses of an individual sleeve and will aid in the invention's purpose of reducing cross-contamination between patients.

The cost of the cover sleeve is low, so that the cover sleeve is used only once and then discarded. The use of a new sterilized disposable cover sleeve each time the medical device is used negates the need to sterilize the medical device after each use.

It should be appreciated by those skilled in the art that the conception and the specific embodiment disclosed might be readily utilized as a basis for modifying or redesigning the medical examination device for carrying out the same purposes as the invention. It should be realized by those skilled in the art that such equivalent constructions do not depart from the spirit and scope of the invention as set forth in the appended claims.

What is claimed is:

1. A cover sleeve comprising:
a cover sleeve body having a first closed end, a second open end, an exterior surface and a lumen, wherein the first closed end of the cover sleeve body is designed to provide a close fit to a distal end of a medical device having an illumination source when the medical device is fully inserted into the lumen of the cover sleeve body; and
a flexible layer integrally attached to the exterior surface of the cover sleeve body having a contact bridge mounted on an underside of the flexible layer facing the lumen of the cover sleeve body, wherein the contact bridge is positioned to physically contact a first contact and a second contact exposed on an outer surface of the medical device when a force is selectably applied to the flexible layer, wherein the physical contact between the contact bridge and the first and second contacts closes a circuit between the first and second contacts and wherein when the force is not applied to the flexible layer the contact bridge does not physically contact the first and second contacts and the circuit open between the first and second contacts.

2. The cover sleeve of claim 1, wherein the circuit closed by the physical contact between the contact bridge and the first and second contacts is an electrical circuit or a magnetic circuit.

3. The cover sleeve of claim 2, wherein the closed circuit actuates the illumination source proximal a distal end of the medical device.

4. The cover sleeve of claim 3, further comprising a transmissive window wherein when the first end of the cover sleeve is installed over the distal end of the medical device the transmissive window overlies the illumination source of the device.

5. The cover sleeve of claim 4, wherein the illumination source emits fluorescent light and the transmissive window is transparent to the emitted light and does not autofluoresce.

6. The cover sleeve of claim 4, wherein the transmissive window is planar and is inclined relative to the longitudinal axis of the cover sleeve.

7. The cover sleeve of claim 4, further comprising an alignment mechanism for ensuring the alignment of the illumination source and the transmissive window.

8. The cover sleeve of claim 1, wherein the cover sleeve is manufactured of a material with a lower thermal conductivity than an outer surface of the medical device.

9. The cover sleeve of claim 1, wherein the cover sleeve and the flexible layer are manufactured of a material with no electrical conductivity and the contact bridge is manufactured of an electrically conductive material.

10. The cover sleeve of claim 1, wherein the cover sleeve body is configured to cover the entire outer axial surface of the medical device when the medical device is fully inserted into the lumen of the cover sleeve.

11. The cover sleeve of claim 10, further comprising a sealable end that is sealingly mounted on the open end of the cover sleeve body when the medical device is fully inserted into the lumen of the cover sleeve.

12. The cover sleeve of claim 11, wherein the sealed cover sleeve provides a protective pathogenic barrier for the medical device.

13. The cover sleeve of claim 1, further comprising an alignment mechanism for ensuring the alignment of the contact bridge with the first and second contact on the outer surface of the medical device.

* * * * *